United States Patent [19]
Shigyo et al.

[11] Patent Number: 5,955,336
[45] Date of Patent: Sep. 21, 1999

[54] DNA SEQUENCE FOR URICASE AND MANUFACTURING PROCESS OF URICASE

[75] Inventors: Tatsuro Shigyo; Kohji Sugihara; Yuji Takamoto; Masachika Takashio; Minoru Kamimura, all of Yaizu; Kazumi Yamamoto, Tsuruga; Yoshio Kojima, Tsuruga; Toshiro Kikuchi, Tsuruga; Shigenori Emi, Tsuruga, all of Japan

[73] Assignee: Toyo Boseki Kabushiki Kaisha, Osaka, Japan

[21] Appl. No.: 07/906,029

[22] Filed: Jun. 26, 1992

Related U.S. Application Data

[63] Continuation-in-part of application No. 07/386,566, Jul. 27, 1989., abandoned

[30] Foreign Application Priority Data

Aug. 17, 1988 [JP] Japan .................................. 63-203239

[51] Int. Cl.⁶ .............................. C12N 9/06; C12N 15/53
[52] U.S. Cl. ........................ 435/191; 435/7.1; 435/320.1; 435/252.3; 536/23.2
[58] Field of Search .............................. 536/23.2; 435/7.1

[56] References Cited

U.S. PATENT DOCUMENTS 3,475,276  10/1969  Kano ........................................ 435/228
4,882,280  11/1989  Takashio et al. ........................ 435/228
4,987,076   1/1991  Takashio et al. ........................ 435/191

FOREIGN PATENT DOCUMENTS 61-280272  6/1985  Japan .

OTHER PUBLICATIONS

Young, et al., "Efficient isolation of genes by using antibody probes", *PNAS,* vol. 80, Mar. 1983, pp. 1194–1198.

Nippon Nogeikagaku Kaishi, vol. 63, No. 3, p. 163 (1989), The Agricultural Society Of Japan, Mar. 15, 1989 and English Language translation thereof.

Cloning a cDNA for Drosphila melanogaster urate oxidase (Gene, vol. 45, 131–173 (1986).

Generation of cDNA Probes Directed by Amino Acid Sequence: Cloning of Urate Oxidase (Science, vol. 239, 1288–1291), date N.A.

Primary structure of the soybean nodulin–35 gene encoding uricase II localized in the peroxisomes of uninfected cells of nodules Proc. Natl. Acad. Sci. vol. 82, 5040–5044, Aug., 1985.

Nucleotide sequence of cDNA and predicted amino acid sequence of rat liver uricase (Eur. J. Biochem. vol. 173 459–463 (1988)).

Suggs et al "Use of synthetic oligonucleotides as hybridization Probes . . . " PNAS vol. 78, No. 11 pp. 6613–6617, 1981.

*Primary Examiner*—Keith D. Hendricks
*Attorney, Agent, or Firm*—Frishauf, Holtz, Goodman, Langer & Chick, P.C.

[57] ABSTRACT

This invention relates to DNA containing a gene encoding uricase, a plasmid having said DNA, a transformant containing said plasmid, and a process for producing uricase by using said transformant.

13 Claims, 7 Drawing Sheets

FIG. 1(A)

```
                                                          10
            ATG ACC AAA CAC AAA GAA AGA GTG ATG TAT TAT GGA
            Met Thr Lys His Lys Glu Arg Val Met Tyr Tyr Gly 20                                          30
AAA GGT GAC GTA TTT GCT TAT CGC ACC TAT TTA AAA CCA CTT ACT GGA GTT AGA
Lys Gly Asp Val Phe Ala Tyr Arg Thr Tyr Leu Lys Pro Leu Thr Gly Val Arg

40
ACG ATT CCT GAA TCT CCA TTT TCC GGT CGA GAT CAT ATT CTT TTT GGA GTA AAT
Thr Ile Pro Glu Ser Pro Phe Ser Gly Arg Asp His Ile Leu Phe Gly Val Asn 50                                  60
GTA AAA ATC TCA GTA GGA GGA ACA AAA TTG CTG ACC TCC TTT ACG AAA GGG GAT
Val Lys Ile Ser Val Gly Gly Thr Lys Leu Leu Thr Ser Phe Thr Lys Gly Asp 70                                  80
AAC AGC TTA GTC GTT GCA ACA GAC TCG ATG AAA AAC TTT ATA CAA AAA CAT TTA
Asn Ser Leu Val Val Ala Thr Asp Ser Met Lys Asn Phe Ile Gln Lys His Leu 90                                  100
GCT AGT TAT ACA GGA ACA ACG ATA GAA GGT TTT TTA GAA TAT GTA GCT ACT TCT
Ala Ser Tyr Thr Gly Thr Thr Ile Glu Gly Phe Leu Glu Tyr Val Ala Thr Ser 110                                 120
TTT TTG AAG AAA TAT TCT CAT ATT GAA AAG ATT TCG TTG ATA GGA GAG GAA ATT
Phe Leu Lys Lys Tyr Ser His Ile Glu Lys Ile Ser Leu Ile Gly Glu Glu Ile

130
CCC TTT GAA ACA ACT TTT GCA GTA AAG AAT GGA AAT AGA GCA GCT AGT GAG CTA
Pro Phe Glu Thr Thr Phe Ala Val Lys Asn Gly Asn Arg Ala Ala Ser Glu Leu 140                                 150
GTA TTT AAA AAA TCA CGA AAT GAA TAT GCC ACC GCT TAT TTG AAT ATG GTT CGT
Val Phe Lys Lys Ser Arg Asn Glu Tyr Ala Thr Ala Tyr Leu Asn Met Val Arg 160                                 170
AAT GAA GAT AAC ACC CTA AAC ATT ACT GAA CAA CAA AGC GGA CTT GCT GGT CTT
Asn Glu Asp Asn Thr Leu Asn Ile Thr Glu Gln Gln Ser Gly Leu Ala Gly Leu 180                                 190
CAA TTA ATA AAA GTC AGC GGA AAT TCC TTT GTC GGT TTT ATT CGT GAC GAA TAC
Gln Leu Ile Lys Val Ser Gly Asn Ser Phe Val Gly Phe Ile Arg Asp Glu Tyr 200                                 210
ACA ACT CTT CCA GAG GAT TCA AAC CGC CCT CTA TTT GTT TAC TTA AAC ATC AAA
Thr Thr Leu Pro Glu Asp Ser Asn Arg Pro Leu Phe Val Tyr Leu Asn Ile Lys

220
TGG AAG TAC AAA AAC ACG GAA GAC TCA TTT GGA ACG AAT CCA GAA AAT TAT GTT
Trp Lys Tyr Lys Asn Thr Glu Asp Ser Phe Gly Thr Asn Pro Glu Asn Tyr Val
```

FIG.1(B)

```
      230                                              240
GCA GCT GAA CAA ATT CGC GAC ATC GCC ACG TCC GTA TTT CAT GAA ACC GAG ACG
Ala Ala Glu Gln Ile Arg Asp Ile Ala Thr Ser Val Phe His Glu Thr Glu Thr
              250                                              260
CTT TCC ATC CAA CAT TTA ATT TAT TTA ATC GGC CGA AGA ATA TTA GAA AGA TTC
Leu Ser Ile Gln His Leu Ile Tyr Leu Ile Gly Arg Arg Ile Leu Glu Arg Phe
                          270                                  280
CCT CAA CTT CAA GAA GTT TAC TTC GAA TCT CAA AAT CAT ACA TGG GAT AAA ATA
Pro Gln Leu Gln Glu Val Tyr Phe Glu Ser Gln Asn His Thr Trp Asp Lys Ile
                                      290                              300
GTG GAG GAA ATT CCT GAA TCA GAA GGG AAA GTA TAT ACA GAA CCG CGA CCG CCA
Val Glu Glu Ile Pro Glu Ser Glu Gly Lys Val Tyr Thr Glu Pro Arg Pro Pro
                                  310
TAT GGA TTT CAA TGC TTT ACT GTC ACC CAA GAA GAC TTG CCA CAC GAA AAC ATT
Tyr Gly Phe Gln Cys Phe Thr Val Thr Gln Glu Asp Leu Pro His Glu Asn Ile
      320                                      330
CTT ATG TTC TCT GAT GAA CCC GAT CAT AAA GGA GCA CTT AAA TGA
Leu Met Phe Ser Asp Glu Pro Asp His Lys Gly Ala Leu Lys ***
```

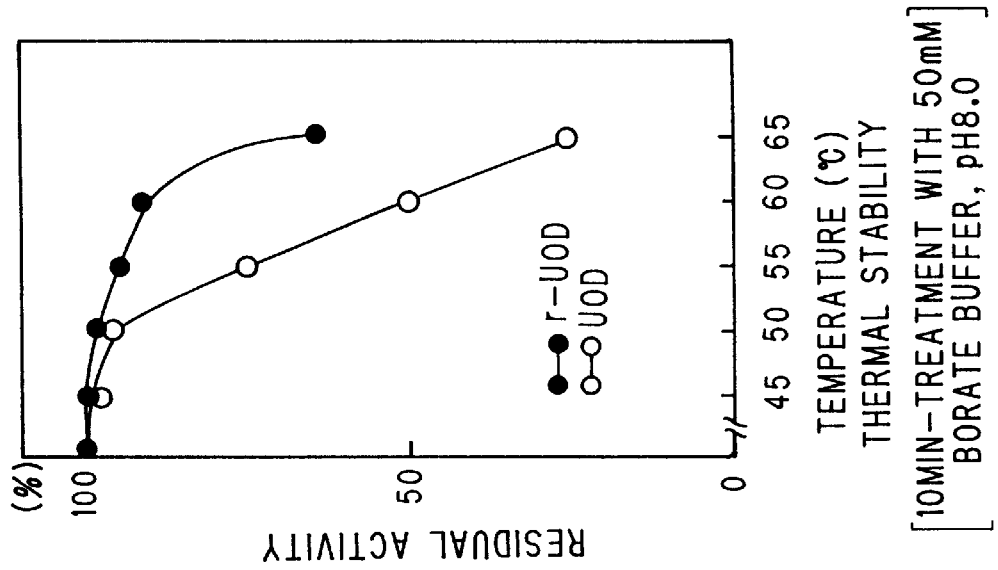
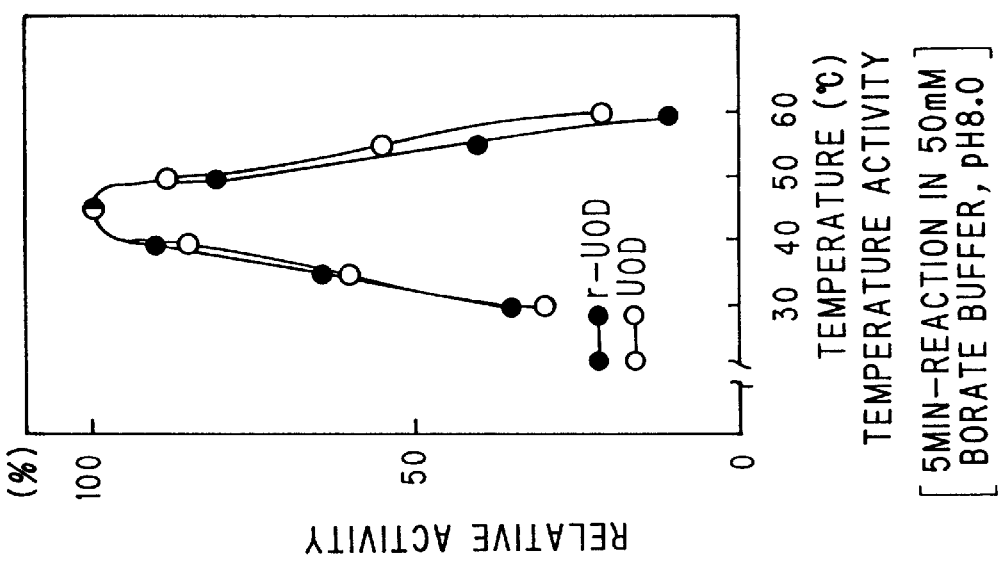

- 94k
- 67k
- 43k
- 30k
- 20k

PAGE OF PURIFIED UOD

DNA SEQUENCE FOR URICASE AND MANUFACTURING PROCESS OF URICASE

CROSS-REFERENCE TO RELATED APPLICATION

This application is a continuation-in-part application of application Ser. No. 07/386,566 filed Jul. 27, 1989, now abandoned.

FIELD OF THE INVENTION

1. Background of the Invention

The present invention relates to a DNA sequence for uricase and the production of uricase. More particularly, this invention relates to a DNA containing a gene encoding uricase, a plasmid having said DNA, a transformant containing said plasmid, and a process for producing uricase by using said transformant.

2. Background Information

Uricase (EC 1, 7, 3, 3) is an enzyme which catalyzes the reaction in which uric acid is hydrolyzed into allantoin, hydrogen peroxide and carbon dioxide, and is useful for assaying uric acid in blood or urine.

Uricase has heretofore been prepared by cultivating an uricase producing microorganism, for example a microorganism belonging to the Genus Canadida in the presence of uric acid in the culture medium and recovering uricase from the culture broth (Japanese Patent Publication No. 5192/1967).

Since this process gives a relatively low yield of uricase, it is desirable to develop a process for producing uricase effectively.

The present inventors have investigated on DNA containing a gene encoding uricase, a plasmid having said DNA, a transformant containing said plasmid and a process for producing uricase by using said transformant. At first, some of the present inventors cloned a uricase gene of thermophilic microorganism, Bacillus sp. TB-90 (FERM BP-795, Japanese Patent Kokai 61-280272) being capable of producing thermally stable uricase, which was isolated from nature by the present inventors, and determined the DNA sequence of said gene. Then, they prepared a plasmid having said DNA, then a transformat containing said plasmid and investigated a process for producing uricase by using said transformant. Thus, the present invention has been established.

SUMMARY OF THE INVENTION

The present invention relates to a DNA containing a gene encoding uricase, a plasmid having said DNA, a transformant having said plasmid and a process for preparing uricase by using said transformant.

The present invention also concerns a uricase which is stable in an aqueous solution at a temperature up to 60° C. and at a pH of 8.0 for 10 minutes. The uricase is also characterized by having a residual activity of at least 90% in an aqueous solution at a pH of 8.0 and at a temperature of 60° C. for 10 minutes. The tests for stability and residual activity are as set forth in Example 3 herein. The uricase is further characterized as originating from Bacillus sp. TB-90 (FERM BP-795). Still further, the uricase has an amino acid sequence as set forth in FIG. 1(A) and FIG. 1(B).

BRIEF DESCRIPTION OF THE DRAWINGS

FIGS. 1(A) and 1(B) show the DNA sequence of a gene encoding uricase originated from Bacillus sp. TB-90 and the corresponding amino acid sequence.

FIG. 6 is a graph of relative activity vs. temperature and which shows the affect of temperature on the activity of uricase.

FIG. 7 is a graph of residual activity vs. temperature and shows the affect of temperature on the stability of uricase.

DETAILED DESCRIPTION OF THE INVENTION

Figure 2:
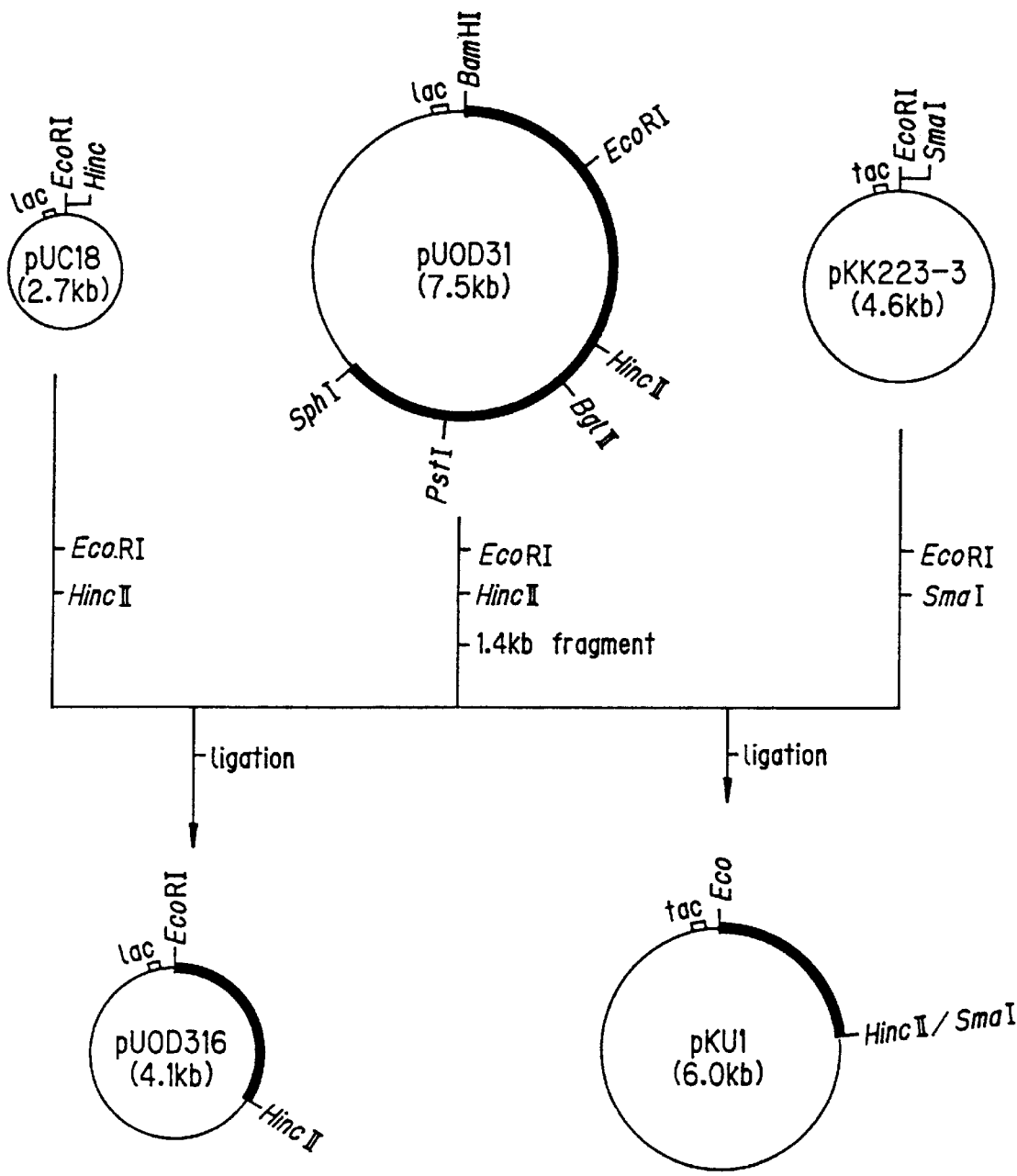
FIG. 2 shows a drawing for constructing expression plasmids pUOD316 and pKU1 from a recombinant plasmid pUOD31 of *E. coli* having a DNA sequence encoding uricase originated from Bacillus sp. TB-90. The black and white boxes show each DNA fragment containing the uricase gene and the region of lac or tac promoter. The ligation means a ligating reaction of DNA fragments by T4 DNA ligase.

The gene encoding uricase in the present invention illustratively includes a gene encoding the following amino acid sequence or having the following nucleotide sequence.

```
                        10                          20
MetThrLysHisLysGluArgValMetTyr TyrGlyLysGlyAspValPheAlaTyrArg 30                          40
ThrTyrLeuLysProLeuThrGlyValArg ThrIleProGluSerProPheSerGlyArg 50                          60
AspHisIleLeuPheGlyValAsnValLys IleSerValGlyGlyThrLysLeuLeuThr 70                          80
SerPheThrLysGlyAspAsnSerLeuVal ValAlaThrAspSerMetLysAsnPheIle 90                         100
GlnLysHisLeuAlaSerTyrThrGlyThr ThrIleGluGlyPheLeuGluTyrValAla 110                         120
ThrSerPheLeuLysLysTyrSerHisIle GluLysIleSerLeuIleGlyGluGluIle
```

```
                      130                              140
ProPheGluThrThrPheAlaValLysAsn GlyAsnArgAlaAlaSerGluLeuValPhe 150                              160
LysLysSerArgAsnGluTyrAlaThrAla TyrLeuAsnMetValArgAsnGluAspAsn 170                              180
ThrLeuAsnIleThrGluGlnGlnSerGly LeuAlaGlyLeuGlnLeuIleLysValSer 190                              200
GlyAsnSerPheValGlyPheIleArgAsp GluTyrThrThrLeuProGluAspSerAsn 210                              220
ArgProLeuPheValTyrLeuAsnIleLys TrpLysTyrLysAsnThrGluAspSerPhe 230                              240
GlyThrAsnProGluAsnTyrValAlaAla GluGlnIleArgAspIleAlaThrSerVal 250                              260
PheHisGluThrGluThrLeuSerIleGln HisLeuIleTyrLeuIleGlyArgArgIle 270                              280
LeuGluArgPheProGlnLeuGlnGluVal TyrPheGluSerGlnAsnHisThrTrpAsp 290                              300
LysIleValGluGluIleProGluSerGlu GlyLysValTyrThrGluProArgProPro 310                              320
TyrGlyPheGlnCysPheThrValThrGln GluAspLeuProHisGluAsnIleLeuMet

330
PheSerAspGluProAspHisLysGlyAla LeuLys

ATGACCAAAC ACAAAGAAAG AGTGATGTAT TATGGAAAAG GTGACGTATT TGCTTATCGC

100
ACCTATTTAA AACCACTTAC TGGAGTTAGA ACGATTCCTG AATCTCCATT TTCCGGTCGA

GATCATATTC TTTTTGGAGT AAATGTAAAA ATCTCAGTAG GAGGAACAAA ATTGCTGACC

200
TCCTTTACGA AAGGGGATAA CAGCTTAGTC GTTGCAACAG ACTCGATGAA AAACTTTATA

300
CAAAAACATT TAGCTAGTTA TACAGGAACA ACGATAGAAG GTTTTTTAGA ATATGTAGCT

ACTTCTTTTT TGAAGAAATA TTCTCATATT GAAAAGATTT CGTTGATAGG AGAGGAAATT

400
CCCTTTGAAA CAACTTTTGC AGTAAAGAAT GGAAATAGAG CAGCTAGTGA GCTAGTATTT

AAAAAATCAC GAAATGAATA TGCCACCGCT TATTTGAATA TGGTTCGTAA TGAAGATAAC

500
ACCCTAAACA TTACTGAACA ACAAAGCGGA CTTGCTGGTC TTCAATTAAT AAAAGTCAGC

600
GGAAATTCCT TTGTCGGTTT TATTCGTGAC GAATACACAA CTCTTCCAGA GGATTCAAAC

CGCCCTCTAT TTGTTTACTT AAACATCAAA TGGAAGTACA AAAACACGGA AGACTCATTT

700
GGAACGAATC CAGAAAATTA TGTTGCAGCT GAACAAATTC GCGACATCGC CACGTCCGTA

TTTCATGAAA CCGAGACGCT TTCCATCCAA CATTTAATTT ATTTAATCGG CCGAAGAATA

800
TTAGAAAGAT TCCCTCAACT TCAAGAAGTT TACTTCGAAT CTCAAAATCA TACATGGGAT

900
AAAATAGTGG AGGAAATTCC TGAATCAGAA GGGAAAGTAT ATACAGAACC GCGACCGCCA

TATGGATTTC AATGCTTTAC TGTCACCCAA GAAGACTTGC CACACGAAAA CATTCTTATG

999
TTCTCTGATG AACCCGATCA TAAAGGAGCA CTTAAATGA
```

The plasmid containing the uricase gene in the present invention can be prepared by construction of a gene library from the chromosomal DNA of said Bacillus sp. TB-90, screening the library with rabbit anti-uricase antibody, isolating DNA fragment containing uricase gene from phage DNA containing the uricase gene of the present invention and ligating it with a vector plasmid.

It is well known that many amino acids are coded by more than one codon. Such base sequence cannot be single but possibly many base sequences may exist. In case of the gene encoding the amino acid sequence of uricase originated from Bacillus sp. TB-90 found by the present inventors, there is a possibility of many DNA base sequences other than the base sequence of the naturally existing gene. Thus, the DNA sequence of the present invention is not only limited to the naturally occurring DNA base sequence but also includes other DNA sequences encoding the amino acid sequence of uricase identified by the present invention.

According to recombinant DNA technique, any artificial variations may take place at a specific region of a fundamental DNA without changing the fundamental properties of what said DNA encodes or so as to improve the properties. Concerning DNA having a the naturally existing base sequence or DNA having a different sequence from the naturally existing one, artificial insertion, deficiency or substitution thereof can be similarly made to provide some genes having properties equivalent to or improved from those of the naturally existing gene. Thus, the present invention includes such modified genes.

An expression vector capable of producing uricase of Bacillus sp. TB-90 in the cells of *Escherichia coli* can be constituted by ligating a gene of uricase of Bacillus sp. TB-90 with appropriate expression vector of *Escherichia coli* such as expression vector pUC18 (Toyobo) retaining lac promoter, expression vector pKK223-3 (Pharmacia) retaining a potent promoter of *Escherichia coli*, naturally tac promoter and terminater of rrnB ribosome RNA, expression vector pDR720 (Pharmacia) retaining trp promoter, inducible expression vector pPL-Lambda (Pharmacia) or the like. Furthermore, it is possible to make a recombinant plasmid capable of producing uricase of Bacillus sp. TB-90 in the cells of *Bacillus subtilis* or in the culture broth by ligating it with vectors, for example, shuttle vector pHY300PLK (Toyobo) between *Bacillus subtilis* and *Escherichia coli*, plasmid vector pUB110 (J. Bacteriol., 134, 318–329, 1978) or the like.

The transformant capable of producing uricase intracellularly or extracellularly can be prepared by introducing the recombinant plasmid retaining uricase gene of the present invention into a host cells such as *Escherichia coli, Bacillus subtilis* or etc.

Uricase can be produced in a large scale by cultivating the transformed microorganism thus obtained in appropriate medium under appropriate conditions. In this case, uricase can be produced effectively for example, by adding an inducer isopropyl thiogalactoside (IPTG) or the like at the early stage of cultivation.

After cultivation, uricase can be isolated, for example, by treating the cells with lysozyme or lysing the cells with supersonic waves or like means or by extraction, separation and purification of the culture broth.

Moreover, not only an *Escherichia coli* or a *Bacillus subtilis* host-vector system but also a Saccharomyces sp., Pseudomonas sp. or a Streptomyces sp. host-vector system may be available. Mass production of uricase can be carried out, depending upon the specific advantage of the respective host-vector systems.

As described in detail above, a DNA sequence and plasmid encoding uricase can be prepared by the present invention, and uricase can be produced by a gene engineering technique. For example, a DNA sequence encoding uricase which is more stable than the uricase conventionally obtained by the known process, a plasmid having such DNA sequence, and the production of uricase by using the transformant containing such plasmid in a gene engineering technique have been available, and so this invention contributes to industrial developments.

The present invention will be explained with reference to the following examples. Any conventional modifications in the technical field of the invention are included within the scope of the present invention.

EXAMPLE 1

Cloning of the uricase gene.

Step 1 Preparation of rabbit anti-uricase antibody

Anti-rabbit anti-uricase antibody antiserum was prepared by administering uricase,obtained by extracting and purifying from the culture broth of Bacillus sp. TB-90 (FERM BP-795), to a rabbit for immunization. The titer of this antiserum was $10^2$ to $10^3$ measured by ELISA method and 16 fold by Ouchterlony method. Then, antiserum was purified by applying 10 ml of antiserum to Protein A Sepharose column chromatography (4 ml), whereby 8.9 ml of anti-uricase antibody Ig G was obtained.

Step 2 Preparation of phage DNA library of Bacillus sp. TB-90

Chromosomal DNA was prepared from 2.5 g of the cell body of Bacillus sp. TB-90 cultivated in the bouillon medium (liquid medium, pH7.2 made by adding 5 g of meat extract, 10 g of peptone and 5 g of sodium chloride and diluting to a volume of 1 L), according to Doi, R. H., (Recombinant Techniques, ed. Rodriquez et al., p162, Addison-Wesley Publishing Company, 1983) or Koizumi, J. et al., (Biotech. Bioeng., 27, 721–728, 1985).

As the result, about 900 μg of considerably pure ($OD_{260}$/$OD_{280}$=about 1.8) chromosomal DNA was obtained. Next, said DNA was partially digested with restriction enzyme Sau3AI in a conventional manner and subjected to 5–20% sucrose density gradient centrifugation to give 2–20 kb fractions of DNA.

One μg of λ phage cloning vector EMBL3 arms (Toyobo) was mixed with 0.4 μg of Sau3AI partially digested chromosomal DNA, ligated with 1 unit of T4 DNA ligase (Toyobo), subjected to packaging with λ DNA using an in vitro packaging kit (Gigapack Gold, Toyobo), to infected *E. coli* Q359 (Toyobo) plated so as to give about 2000 plagues per plate.

Step 3 Selection of recombinant phages containing the gene for the uricase (Isolation of uricase gene clone by plaque hybridization)

Said purified IgG was mixed with horseradish peroxidase (HRPO) to give IgG-HRPO conjugate. The uricase gene clone was isolated by using a Gene Expression kit (Boehringer Manheim) with the conjugate. In this case the detection sensitivity was 100 pg DNA. Said phage DNA library was screened to give bluish green-colored positive clones, and then strongly colored clone was selected and the phage was purified until all the plaques colored. As the result, phages 1 and 3 were selected, infected with *E. coli* Q359, and the supernatant of each culture broth was asayed for uricase activity, allowing 7 mU/ml and 9 mU/ml, respectively.

Identification of the uricase gene of Bacillus sp. TB-90

Phage DNAs of isolated positive clones 1 and 3 were prepared in a conventional method (Molecular Cloning, ed. Maniatis et al., p. 85, Cold Spring Harbor Laboratory U.S.A., 1982), digested with restriction enzymes BamHI and SalI and analyzed by 0.8% agarose gel electrophoresis, showed that 18 kb and 15 kb SalI DNA fragments were inserted in DNAs from phages 1 and 3, respectively.

Further, a restriction map of inserted DNA using BamHI, SphI and KpnI, showed that phage 1 contained phage 3 and both had a common region. Then phage DNA of phage 1 was digested with restriction enzyme SalI, and 18 kb inserted DNA fragment was extracted from agarose gel (Yoshiyuki Sakaki, Vector DNA, p.67, Kohdansha, Southern hybridization analysis, using the 18 kb fragment as a probe (J.Mol, Biol., 98, 503–517, 1975), showed that the 18 kb DNA fragment of phage 1 was hybridized with not only the 15 kb DNA fragment of phage 3 but also with the chromosomal DNA of TB-90 strain. This fact indicated that the phage 1 DNA and the phage 3 DNA, that had uricase activity, contained a common region and had an inserted DNA fragment derived from the chromosomal DNA of Bacillus sp. TB-90.

Then, the 15 kb DNA fragment was isolated from phage 3 DNA in the same method as described above, ligated with SalI-digested plasmid vector pUC18, subcloned and the uricase gene region was specified in the insertion DNA fragment to give a recombinant plasmid named pUOD31, having 4.8 kb BamHI-SphI fragment containing uricase gene. The restriction map of this plasmid is shown at the upper center of FIG. 2.

Subsequently, the DNA fragment which was digested with various restriction enzymes was subcloned into vectors pUC18 and 19, and the plasmid DNA was prepared according to Birnboim and Doly (Nucleic Acids Res., 7, 1513–1523, 1979). The resulting DNA was suspended in 18 µl of TE (10 mM Tris-hydrochloric acid(pH7.4), 1 mM EDTA), mixed with 2 µl 2N NaOH, allowed to stand at room temperature for 5 minutes, mixed with 8 µl of 5M ammonium acetate and mixed with 100 µl of cold ethanol for ethanol precipitation. Determination of base sequence on these plasmid DNAs was performed with M13 sequencing kit (Toyobo) and [α-32p] dCTP (400 Ci/mmol, Amersham Japan).

FIG. 1 shows the determined sequence. The uricase gene originated from Bacillus sp TB-90 had a 999 bases coding region starting from an initiation codon ATG and ending in a stop codon TGA, which encoded 332 amino residues as shown in FIG. 1.

Construction of expression plasmid pUOD316 and pKU1 for the purpose of expressing uricase gene of Bacillus sp. TB-90 in the cells of *Escherichia coli*

About 10 µg of recombinant plasmid pUOD31 containing uricase gene was mixed with EcoRI and HincII, allowed to react at 37° C. for 2 hours in 30 µl of M buffer (10 mM Tris-HCl (pH7.5), 10 mM MgCl$_2$, 1 mM dithiothreitol and 50 mM NaCl), and the reaction mixture was subjected to electrophoresis with 0.8% agarose gel containing 0.1 µg/ml of ethidium bromide, to isolate 1.4 kb of EcoRI-HincII DNA fragment.

Then, 1 µg of expression vectors pUC18 (Toyobo) or pKK223-3 (Pharmacia) were digested with EcoRI, HincII and with EcoRI, SmaI, respectively, to isolate 2.7 kb and 4.6 kb of the DNA fragments were isolated in the same method as described above, respectively.

Subsequently, 1 µg of the 1.4 kb EcoRI-HincII DNA fragment intially prepared was mixed with each 1 µg of expression vector pUC18 or pKK223-3, respectively mixed with 5 units of T4DNA ligase (Toyobo) and allowed to react at 16° C. for 6 hours in 45 µl of ligase reaction buffer (66 mM Tris-HCl (pH 7.6), 6.6 mM MgCl$_2$, 10 mM dithiothreitol and 1.0 mM ATP).

Then, *Escherichia coli* JM109 (Takara Shuzo) was transformed with the reaction mixture of ligation according to Hanahan's method, (J. Mol. Biol., 166, 557, 1983). Ampicillin resistant colonies appeared were cultivated in L-broth solid medium [10 g of trypton (Difco), 5 g of yeast extract (Difco), 5 g of NaCl, and a medium (pH7.2) prepared by dissolving 15 g of powdery agar in 1 L of distilled water] containing 50 µg/ml of ampicillin, and plasmid DNA was prepared by the method of Birnboim and Doly and digested with various restriction enzymes. The restriction fragment analysis on agarose gel electrophoresis showed correct insertion of 1.4 kb EcoRI-HincII DNA fragments into the respective expression vectors. The recombinant plasmid ligated with pUC18 was called pUOD316, and those ligated with pKK223-3 was called pKU1. FIG. 2 shows the construction method of expression plasmids pUOD316 and pKU1 from recombinant plasmid pUOD31.

Production of uricase in *Escherichia coli*

Each expression plasmid pUOD316 or pKU1 thus constructed was introduced into *Escherichia coli* JM109 according to Hanahan's method, and each uricase produced by recombinant *E. Coli* JM109/pUOD316 and JM109/pKU1, respectively was identified and analyzed as shown below.

Each recombinant *E. coli* was cultivated overnight at 37° C. in L broth liquid medium. 0.1 ml of culture broth was transferred to 10 ml of L broth liquid medium and cultivated at 37° C. When OD$_{660}$ reached at 0.2, isopropylthiogalactoside (IPTG) was added to a final concentration of 1 mM. After the cultivation was further continued for 16 hours, 1.0 ml of the culture broth was separated, mixed with 0.5 ml of extraction buffer [50 mM borate buffer (pH8.0), 10 mM EDTA·3Na, 0.3% Triton X-100, and 0.3% lysozyme], incubated at 37° C. for 10 minutes and centrifuged at 12,000 rpm for 10 minutes to give a bacteriolyticlysate (supernatant). Twenty µl of this lysate was suspended in the same amount of sample loading buffer [62.5 mM Tris-HCl (pH6.8), 2% SDS, 10% glycerol, 5% 2-mercaptoethanol, and 0.001% BPB], heated at 100° C. for 5 minutes and subjected to SDS-polyacrylamide gel electrophoresis according to Laemmli et al., (Nature, 227, 680–685, 1970). After the electrophoresis, the gel was stained with Coomassie brilliant blue, destained, dried and fixed on a filter paper. As the result, an uricase band of about 35K molecular weight was detected on *E. coli* JM109 containing expression plasmid, and this protein band showed specific binding with anti-uricase antibody (IgG). When each protein band on the gel was measured with a densitometer, it was found that each 1% and 3% of uricase per whole intracellular protein was produced by *E. coli* JM109/pUOD316 and JM109/pKU1. These results showed that these recombinant *E. coli* produced efficiently uricase of Bacillus sp. TB-90. *E. coli* JM109/pUOD316 was deposited as FERM BP-1979 and *E. coli* JM109/pKU1 as FERM BP-1980 in Fermentation Research Institute, Agency of Industrial Science and Technology, Ministry of International Trade and Industry, respectively. Uricase thus obtained above has the following characteristics.

(1) Reactivity:
Uricase catalyzes the reaction in which uric acid is decomposed oxidatively to release hydrogen peroxide.
(2) Optimum pH
5–10
(3) Stable pH
5–9
(4) Optimum temperature
45–50° C.
(5) Stable temperature range
No less than uricase activity is observed when it is treated at 50° C. for 10 minutes.
(6) Substrate specificity
Uricase shows substrate specificity to uric acid.

EXAMPLE 2

Construction of recombinant plasmid pEB2 for expression of uricase gene in *Bacillus subtilis*

3.0 kb BamHI-BglII fragment containing uricase gene was isolated and extracted from *E. coli* recombinant plasmid pUOD31 as prepared in the same method as in Example 1.

Figure 3:
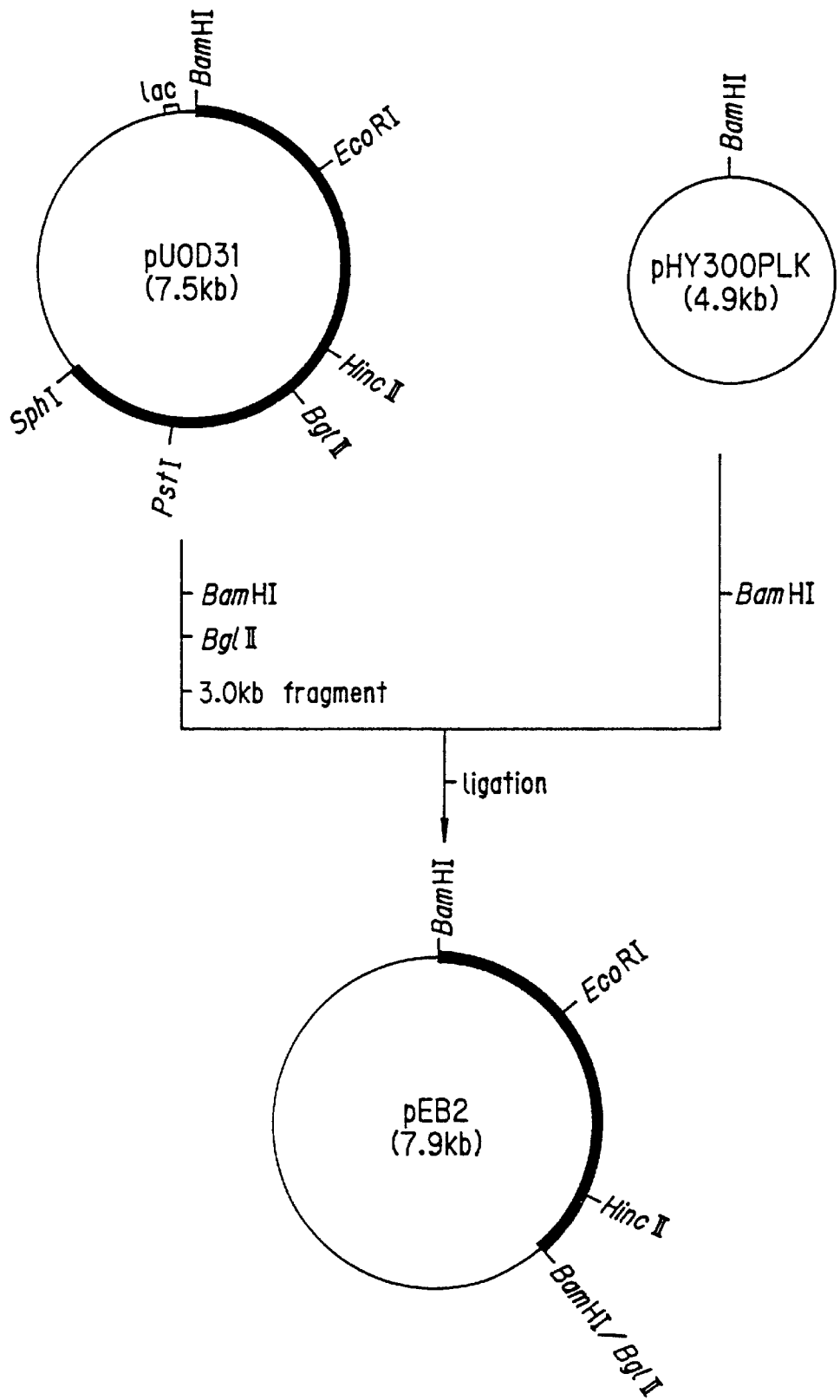
FIG. 3 shows a drawing for constructing a recombinant plasmid pEB2 of *Bacillus subtilis* having a DNA sequence encoding uricase originated from Bacillus sp. TB-90. The black and white boxes and ligation have the same meanings as described in FIG. 2.

Then, 2 μg of E. coli-Bacillus subtilis shuttle vector pHY300 PLK(Toyobo) was digested with restriction enzyme BamHI, ligated with 2 μg of 3.0 kb BamHI-BglII fragment containing uricase gene by using 2 units of T4 DNA ligase, and E. coli C600 was transformed according to Hanahan's method. An ampicillin resistant strain was selected on L broth solid medium. Plasmid DNA was prepared from C600 strain showing uricase activity among the transformed strains according to the method of Birnboim et al named pEB2. FIG. 3 shows a constructing method of this plasmid. Then competent cells of Bacillus subtilis ISW 1214 (Toyobo) were transformed with this plasmid according to Rodriguez et al., ed., (Recombinant DNA Techniques, p.184–186, Addison-Wesley Publishing Company, 1983). These cells were plated on L broth solid medium containing 15 μg/ml of tetracycline and 0.2% glucose and cultivated at 37° C. overnight. As the result, Bacillus subtilis transformed with recombinant plasmid pEB2 was obtained by selecting a tetracycline resistant colonies. This transformant was cultivated at 37° C. overnight in L broth liquid medium containing 15 μg/ml of tetracycline and 0.2% glucose, and the plasmid was isolated and extracted according to Rodriguez et al., (Recombinant DNA Techniques, ed., p. 164–165, Addison-Wesley Publishing Company, 1983). The plasmid of this transformant was digested with various restriction enzymes and subjected to electrophoresis on agarose gel, whereby it was confirmed that this plasmid retained the recombinant plasmid pEB2 in which 3.0 kb BamHI-BglII fragment containing uricase gene was inserted.

Production of uricase in the cells of Bacillus subtilis

Uricase, produced by recombinant Bacillus subtilis ISW1214/pEB2 (FERM BP-1981) which was obtained by introducing recombinant plasmid pEB2 containing uricase gene into Bacillus subtilis ISW 1214, was identified and analyzed as shown below.

Recombinant Bacillus subtilis was cultivated at 37° C. overnight in L broth liquid medium containing 15 μg/ml of tetracycline and 0.2% glucose. After cultivation, 1.0 ml of the culture broth was separated and centrifuged at 8,000 rpm for 5 minutes, to separate supernatant from the cells. The cells were suspended in 1.0 ml of extraction buffer, incubated at 37° C. for 10 minutes and centrifuged at 12,000 rpm for 10 minutes to give a cell lysate. Then, each 20 μl of the culture supernatant and the cell lysate was suspended in the same amount of said sample loading buffer, heated at 100° C. for 5 minutes and subjected to electrophoresis on SDS-polyacrylamide gel according to Laemmli et al. method. After electrophoresis, the gel was stained with Coomassie brilliant blue, destained, dried and fixed on a filter paper. As the result, it was found that a band of uricase in about 35K of molecular weight was detected in both the culture supernatant and the cell lysate of Bacillus subtilis ISW 1214 transformant containing pEB2, and this protein band showed a specific cross reaction with anti-uricase antibody (IgG). When each protein band was assayed by a densitometer, Bacillus subtilis ISW 1214/pEB2 produced 0.6% of uricase per whole cellular protein in the cells. Further, 40% of uricase produced in the cells was found to be secreted to the culture supernatant, namely extracellularly. Accordingly, it was found that recombinant Bacillus subtilis ISW 1214/pEB2 produced uricase intracellularly or extracellularly.

EXAMPLE 3

The following physicochemical properties were measured for uricase obtained by Example 1 (hereinafter referred to as "r-UOD") and the uricase produced by Bacillus sp. TB-90 (a product of Sapporo Breweries Limited; hereinafter referred to as "UOD").

The following method was employed in order to measure the activity.

The activity determination of the uricase was performed in most cases by the UV method described below utilizing the decrease in the ultraviolet absorption of uric acid at a wavelength of 293 nm. The activity of the uricase is defined by taking a titer of the enzyme decomposing 1 μmole of uric acid for 1 minute under the conditions of determination given below as 1 U (unit). The activity in U/ml was calculated using the equation below:

Activity of uricase, U/ml $$\frac{\Delta OD \times (\text{overall volume of solution, ml}) \times (\text{times dilution})}{12.2 \times (\text{reaction time, minutes}) \times (\text{volume of enzyme solution, ml})}$$

in which $\Delta OD$ is the decrease in the optical density at 293 nm during the reaction and 12.2 is the molecular extinction coefficient of uric acid given in $cm^2$/micromole.

Figure 4:
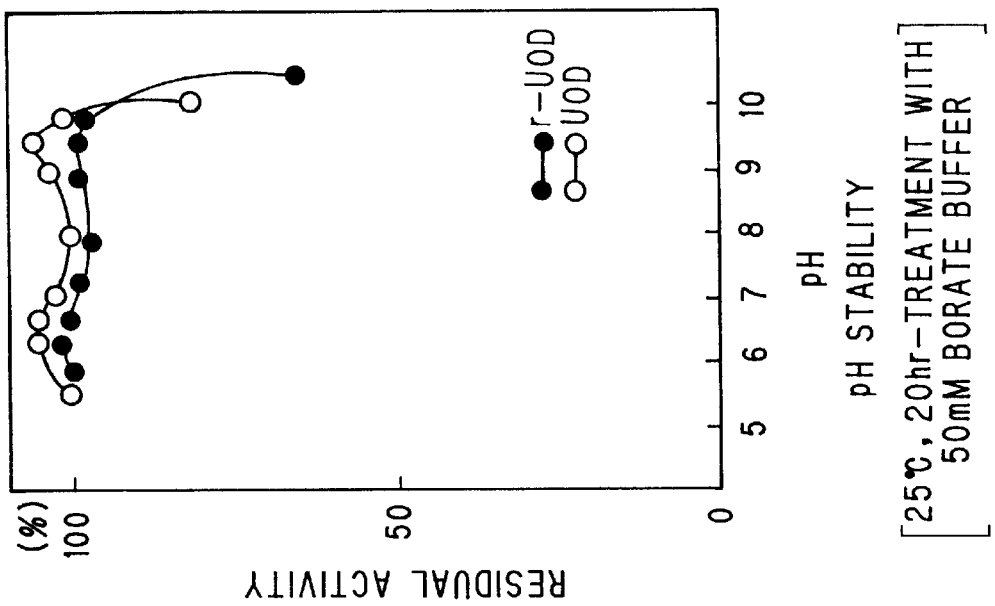
FIG. 4 is a graph of relative activity vs. pH and shows the effect of pH on the activity of uricase.

(1) Optimum pH (Effect of pH on activity):

Each enzyme in such an amount as to attain 10 mU/ml at a pH of 8.0 and 37° C. was dissolved and allowed to react in buffers having various pHs shown in FIG. 4.

The uric acid concentration was set to 100 μM, and a 50 mM boric acid buffer (1 mM EDTA·2Na and 0.001% "TRITON X-100") was used as the buffer. The reaction was carried out at 37° C., and while the solution was stirred and mixed in a cuvette, the decrease of the absorbance (293 μm) was measured (UV method).

FIG. 4 shows the relative activity at each pH with respect to the pH, at which each enzyme exhibited the highest activity, being 100.

As can be seen clearly from FIG. 4, the optimum pH was 5 to 10, especially near 9 for both of the enzymes.

Figure 5:
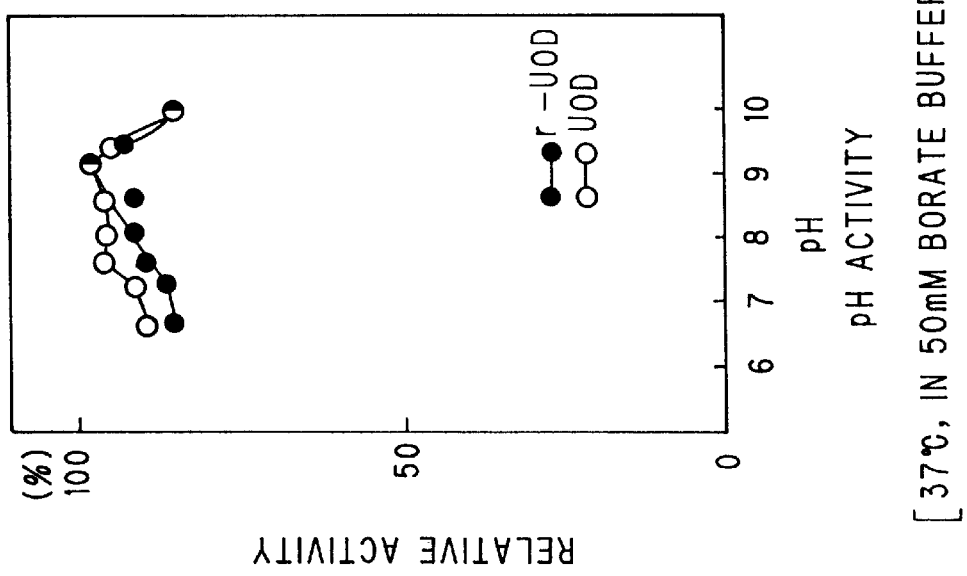
FIG. 5 is a graph of residual activity vs. pH and concerns pH stability of uricase.

(2) Stable pH range:

The enzymes were dissolved in such amounts as to attain 200 mU/ml (measured at 30° C. and pH 8.0) in 50 mM boric acid buffers having various pHs (mM EDTA·2Na and 0.001% "TRITON X-100") shown in FIG. 5.

Next, after each of the enzyme solutions was held at 25° C. for 20 hours, each was diluted 20 times with the 50 mM boric acid buffer (pH 8.0, 1 mM EDTA·2Na and 0.001% "TRITON X-100"). While the pH was kept near 8.0, 100 μM uric acid was added to each of the enzyme solutions and was allowed to react at 30° C. The enzyme activity was measured by the UV method, and FIG. 5 shows the relative residual activity at each pH when the activity at the start of the test (that is, at the time of non-treatment) was 100.

As can be seen clearly from FIG. 5, both enzymes maintained their activity between pH 5 and 9.

(3) Optimum temperature (Effect of temperature on activity):

Each enzyme was dissolved in such an amount as to attain 10 mU/ml in 50 mM boric acid buffer (pH 8.0, 1 mM EDTA·2Na and 0.001% "TRITON X-100"), and 100 μM of uric acid was allowed to react as the substrate. The reaction time was 5 minutes and measurement was made by the UV method.

FIG. 6 shows the relative activity at each temperature when the temperature providing the highest activity was 100.

As can be seen clearly from FIG. 6, the optimum temperature was found to be within the range of 45 to 50° C. for both enzymes.

(4) Heat stability (Effect of temperature on stability):

Each enzyme was dissolved in 100 μl of boric acid buffer (pH 8.0, 1 mM EDTA·2Na and 0.001% "TRITON X-100"), and the solution was kept at each temperature shown in FIG. 7 for 10 minutes. After each solution was diluted 100 times, the temperature was changed to 37° C. and the residual activity was measured by the UV method (pH 8.0, uric acid 100 pM).

FIG. 7 shows the relative activity at each temperature when the enzyme activity of non-treatment was 100.

As can be seen clearly from FIG. 7, whereas UOD was quickly inactivated when the temperature exceeded 50° C., r-UOD of the present invention maintained its activity up to about 60° C.

(5) Molecular weight: (measurement method)

2 mg of the enzyme was dissolved in 1 ml of distilled water and the solution was subjected to SDS gel electrophoresis. The gel after this electrophoresis was dyed with Cumer Brilliant Blue (CBB).

Figure 8A:
FIG. 8 are photographs showing the results of Native-PAGE (FIG. 8A), Western blotting (FIG. 8B) and SDS-PAGE (FIG. 8C) for purified uricase.
Figure 8B:
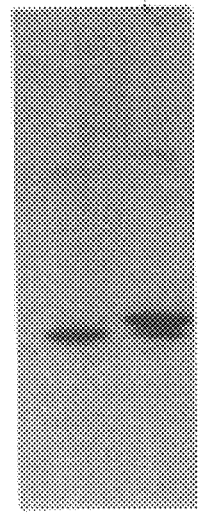
Figure 8C:
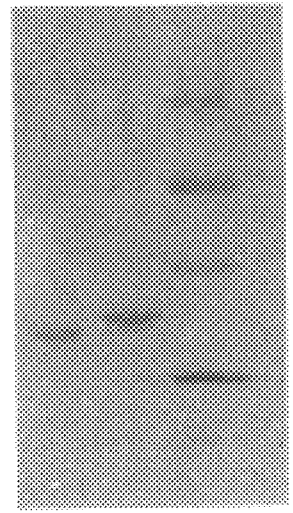

Result:

As shown in FIG. 8, whereas UOD exhibited a molecular weight of about 32,000 Daltons, r-UOD exhibited a molecular weight of about 35,000 Daltons. It was thus found out that there was a difference of the molecular weight in the sub-unit.

(6) Identification of amino acid sequence: (measurement method)

500 pmol of each enzyme was tested by "477A type protein sequencer" of ABI Co. and its N terminal end sequence was determined.

The C terminal end amino acid sequence was determined for the similar samples by the use of carboxypeptidases A and B.

Result:

The N terminal end 28 amino acid was in perfect agreement with the amino acid sequence anticipated from the DNA sequence for both of UOD and r-UOD. As to the C terminal end sequence, however, the C terminal end sequence of r-UOD was in agreement with the C terminal end sequence anticipated from the DNA sequence, but the C terminal end sequence of UOD was in agreement with the sequence upstream of the 13 amino acid residue from the C terminal end anticipated from the DNA sequence. This presumably represents that in the UOD, after the protein containing the 332 amino acid residue was synthesized, the 13 amino acid residue was cut off on the C terminal end side inside the cells of Bacillus sp. TB-90.

(7) Reactivity:

Uricase catalyzes the reaction in which uric acid is decomposed oxidatively to release hydrogen peroxide.

(8) Substrate specificity:

Uricase shows substrate specificity to uric acid.

What is claimed is:

1. A sequence derived from Bacillus sp. TB-90 (FERM BP-795), which encodes an uricase having the following amino acid sequence:

```
                                        10
            MetThrLysHisLysGluArgValMetTyr

20
            TyrGlyLysGlyAspValPheAlaTyrArg

30
            ThrTyrLeuLysProLeuThrGlyValArg

40
            ThrIleProGluSerProPheSerGlyArg

50
            AspHisIleLeuPheGlyValAsnValLys

60
            IleSerValGlyGlyThrLysLeuLeuThr

70
            SerPheThrLysGlyAspAsnSerLeuVal

80
            ValAlaThrAspSerMetLysAsnPheIle

90
            GlnLysHisLeuAlaSerTyrThrGlyThr

100
            ThrIleGluGlyPheLeuGluTyrValAla

110
            ThrSerPheLeuLysLysTyrSerHisIle

120
            GluLysIleSerLeuIleGlyGluGluIle

130
            ProPheGluThrThrPheAlaValLysAsn

140
            GlyAsnArgAlaAlaSerGluLeuValPhe

150
            LysLysSerArgAsnGluTyrAlaThrAla

160
            TyrLeuAsnMetValArgAsnGluAspAsn

170
            ThrLeuAsnIleThrGluGlnGlnSerGly

180
            LeuAlaGlyLeuGlnLeuIleLysValSer

190
            GlyAsnSerPheValGlyPheIleArgAsp

200
            GluTyrThrThrLeuProGluAspSerAsn

210
            ArgProLeuPheValTyrLeuAsnIleLys

220
            TrpLysTyrLysAsnThrGluAspSerPhe

230
            GlyThrAsnProGluAsnTyrValAlaAla

240
            GluGlnIleArgAspIleAlaThrSerVal

250
            PheHisGluThrGluThrLeuSerIleGln

260
            HisLeuIleTyrLeuIleGlyArgArgIle

270
            LeuGluArgPheProGlnLeuGlnGluVal

280
            TyrPheGluSerGlnAsnHisThrTrpAsp

290
            LysIleValGluGluIleProGluSerGlu

300
            GlyLysValTyrThrGluProArgProPro

310
            TyrGlyPheGlnCysPheThrValThrGln

320
            GluAspLeuProHisGluAsnIleLeuMet

330
            PheSerAspGluProAspHisLysGlyAla

LeuLys.
```

2. The DNA sequence according to claim 1, which has the following DNA sequence:

```
ATGACCAAAC ACAAAGAAAG AGTGATGTAT TATGGAAAAG GTGACGTATT TGCTTATCGC
                                100
ACCTATTTAA AACCACTTAC TGGAGTTAGA ACGATTCCTG AATCTCCATT TTCCGGTCGA

GATCATATTC TTTTTGGAGT AAATGTAAAA ATCTCAGTAG GAGGAACAAA ATTGCTGACC
                200
TCCTTTACGA AAGGGGATAA CAGCTTAGTC GTTGCAACAG ACTCGATGAA AAACTTTATA
                                                            300
CAAAAACATT TAGCTAGTTA TACAGGAACA ACGATAGAAG GTTTTTTAGA ATATGTAGCT

ACTTCTTTTT TGAAGAAATA TTCTCATATT GAAAAGATTT CGTTGATAGG AGAGGAAATT
                                400
CCCTTTGAAA CAACTTTTGC AGTAAAGAAT GGAAATAGAG CAGCTAGTCA GCTAGTATTT

AAAAAATCAC GAAATGAATA TGCCACCGCT TATTTGAATA TGGTTCGTAA TGAAGATAAC
                500
ACCCTAAACA TTACTGAACA ACAAAGCGGA CTTGCTGGTC TTCAATTAAT AAAAGTCAGC
                                                            600
GGAAATTCCT TTGTCGGTTT TATTCGTGAC GAATACACAA CTCTTCCAGA GGATTCAAAC

CGCCCTCTAT TTGTTTACTT AAACATCAAA TGGAAGTACA AAAACACGGA AGACTCATTT
                                700
GGAACGAATC CAGAAAATTA TGTTGCAGCT GAACAAATTC GCGACATCGC CACGTCCGTA

TTTCATGAAA CCGAGACGCT TTCCATCCAA CATTTAATTT ATTTAATCGG CCGAAGAATA
                800
TTAGAAAGAT TCCCTCAACT TCAAGAAGTT TACTTCGAAT CTCAAAATCA TACATGGGAT
                                                            900
AAAATAGTGG AGGAAATTCC TGAATCAGAA GGGAAAGTAT ATACAGAACC GCGACCGCCA

TATGGATTTC AATGCTTTAC TGTCACCCAA GAAGACTTGC CACACGAAAA CATTCTTATG
                                999
TTCTCTGATG AACCCGATCA TAAAGGAGCA CTTAAATGA.
```

3. A plasmid comprising the DNA sequence according to claim 2.

4. A microbial host transformed by the plasmid according to claim 3.

5. A process for the preparation of uricase comprising culturing the transformed microbial host of claim 4 under conditions suitable for the expression of uricase and recovering uricase.

6. A plasmid comprising the DNA sequence according to claim 1.

7. A microbial host transformed by the plasmid according to claim 6.

8. A process for the preparation of uricase comprising culturing the transformed microbial host of claim 7 under conditions suitable for the expression of uricase and recovering uricase.

9. A microbial transformed host, in which the host is *Escherichia coli* JM109 (pUOD316), *Escherichia coli* JM109 (pKU1) or *Bacillus subtilis* ISW 1214 (pEB2).

10. A process for the preparation of uricase comprising culturing the transformed microbial host of claim 9 under conditions suitable for the expression of uricase and recovering uricase.

11. A process for producing a plasmid containing the DNA encoding the uricase having the amino acid sequence set forth in claim 1, comprising
 (a) constructing a gene library from chromosomal DNA of Bacillus sp. TB-90 (FERM BP-795),
 (b) screening said library with rabbit anti-uricase antibody, said antibody produced by immunizing rabbits with purified uricase,
 (c) isolating a DNA fragment containing the DNA encoding said uricase from said library,
 (d) isolating the DNA encoding said uricase from the DNA fragment and
 (e) ligating the DNA encoding said uricase with a vector plasmid.

12. The process according to claim 11, wherein the chromosomal DNA of Bacillus sp. TB-90 (FERM BP-795) is partially digested with a restriction enzyme and the partially digested chromosomal DNA is ligated into phage cloning vectors.

13. The process according to claim 12, wherein said uricase gene is ligated with a vector plasmid selected from the group consisting of pUOD31, pKU1 and pEB2.

* * * * *